(12) United States Patent
Nicolas et al.

(10) Patent No.: US 12,629,479 B2
(45) Date of Patent: May 19, 2026

(54) MEDICAL INJECTION SYSTEM

(71) Applicant: Becton Dickinson France, Le Pont de Claix Cedex (FR)

(72) Inventors: Maxime Nicolas, Grenoble (FR); Michael Fiard, Corenc (FR); Gilles Bernede, Arbusigny (FR)

(73) Assignee: Becton Dickinson France, Le Pont de Claix (FR)

( * ) Notice: Subject to any disclaimer, the term of this patent is extended or adjusted under 35 U.S.C. 154(b) by 953 days.

(21) Appl. No.: 17/289,371

(22) PCT Filed: Nov. 15, 2019

(86) PCT No.: PCT/EP2019/081465
§ 371 (c)(1),
(2) Date: Apr. 28, 2021

(87) PCT Pub. No.: WO2020/104315
PCT Pub. Date: May 28, 2020

(65) Prior Publication Data
US 2021/0393886 A1 Dec. 23, 2021

(30) Foreign Application Priority Data
Nov. 19, 2018 (EP) ..................................... 18207116

(51) Int. Cl.
| | |
|---|---|
| *A61M 5/315* | (2006.01) |
| *A61M 5/31* | (2006.01) |
| *A61M 5/32* | (2006.01) |

(52) U.S. Cl.
CPC ...... *A61M 5/31571* (2013.01); *A61M 5/3135* (2013.01); *A61M 5/31505* (2013.01);
(Continued)

(58) Field of Classification Search
CPC .......... A61M 5/31571; A61M 5/31505; A61M 5/3257; A61M 5/3271; A61M 5/31573;
(Continued)

(56) References Cited

U.S. PATENT DOCUMENTS

| | | | |
|---|---|---|---|
| 8,696,628 B2 * | 4/2014 | Grunhut | ........... A61M 5/31501 604/110 |
| 9,789,264 B2 * | 10/2017 | Roberts | ................. A61M 5/326 |

(Continued)

FOREIGN PATENT DOCUMENTS

| | | | | |
|---|---|---|---|---|
| WO | WO-2006111860 A1 * | 10/2006 | .......... | A61M 5/2033 |

*Primary Examiner* — Michael J Tsai
*Assistant Examiner* — Forrest Blake Dipert
(74) *Attorney, Agent, or Firm* — The Webb Law Firm

(57) ABSTRACT

A medical injection system comprising: a syringe provided with a barrel, a stopper and an injection needle; a plunger rod which engages with the stopper; an injection lock preventing relative movement of the plunger rod with respect to the barrel; and a needle guard comprising a trigger portion and configured to slidably engage the barrel so as to define a first position covering the injection needle and a second position not covering a predetermined portion of the injection needle.

(Continued)

The trigger portion is adapted to disengage the injection lock from the plunger rod when the needle guard moves from the first position to the second position.

14 Claims, 6 Drawing Sheets

(52) U.S. Cl.
CPC ........ *A61M 5/3204* (2013.01); *A61M 5/3245* (2013.01); *A61M 5/3257* (2013.01); *A61M 2005/3131* (2013.01); *A61M 2005/3247* (2013.01); *A61M 2005/3267* (2013.01); *A61M 5/3271* (2013.01)

(58) Field of Classification Search
CPC .......... A61M 5/31576; A61M 5/31578; A61M 2005/3247; A61M 2005/3258; A61M 2005/3263; A61M 2005/3267; A61M 2005/31508
See application file for complete search history.

(56) References Cited

U.S. PATENT DOCUMENTS

| | | | | |
|---|---|---|---|---|
| 2004/0215151 | A1* | 10/2004 | Marshall | A61M 5/322 |
| | | | | 604/198 |
| 2004/0225262 | A1* | 11/2004 | Fathallah | A61M 5/326 |
| | | | | 604/110 |
| 2009/0318864 | A1* | 12/2009 | Carrel | A61M 5/3272 |
| | | | | 604/117 |
| 2011/0092915 | A1* | 4/2011 | Olson | A61M 5/3243 |
| | | | | 604/198 |
| 2012/0203186 | A1* | 8/2012 | Vogt | A61M 5/3204 |
| | | | | 604/192 |
| 2014/0257184 | A1* | 9/2014 | Carrel | A61M 5/3287 |
| | | | | 604/117 |
| 2015/0190580 | A1* | 7/2015 | Imai | A61M 5/31505 |
| | | | | 604/220 |
| 2017/0043105 | A1 | 2/2017 | Elmen | |
| 2017/0106146 | A1* | 4/2017 | Folk | A61M 5/3245 |
| 2019/0298934 | A1* | 10/2019 | Saussaye | A61M 5/326 |
| 2021/0093787 | A1* | 4/2021 | Perot | A61M 5/178 |

* cited by examiner

1

1

MEDICAL INJECTION SYSTEM

CROSS-REFERENCE TO RELATED APPLICATIONS

This application is the United States national phase of International Application No. PCT/EP2019/081465 filed Nov. 15, 2019, and claims priority to European Patent Application No. 18207116.7 filed Nov. 19, 2018, the disclosures of which are hereby incorporated by reference in their entirety.

BACKGROUND OF THE INVENTION

Field of the Invention

The present invention relates to a medical injection system for self-administration of a drug composition.

Description of Related Art

Medical injection systems allowing self-administration of a drug composition have been developed so that patients having non-curable or long-term diseases can administer their own drug composition without the need of any medical staff. Consequently, these medical injection systems usually provide a simplified operation, for example by combining several steps into a single distal movement.

Such a medical injection system is usually provided in a position in which the injection needle intended to deliver the drug composition is hidden or covered within the medical injection system and can perform at least the following steps:

a first step of needle pricking, i.e. inserting the injection needle into the patient's body, a second step of injection, i.e. injecting or delivering the drug composition through the injection needle into the patient's body.

However, a problem may occur in that the injection step is triggered before the end of the needle pricking step so that the injection needle may not be inserted into the patient's body or may be inserted at an inappropriate depth of the patient's skin. Such a failed administration often results in wasting valuable drug composition and is inconvenient for the patient.

The purpose of the present disclosure is to solve the above-mentioned problem in order to propose a medical injection system of a low cost and simple operation, and able to minimize the number of failed administrations.

SUMMARY OF THE INVENTION

This objective is accomplished by a medical injection system comprising:

(a) a syringe provided with:
(i) a barrel having a proximal edge;
(ii) a stopper in sliding engagement inside the barrel; and
(iii) an injection needle;
(b) a plunger rod in pushing engagement with the stopper
(c) an injection lock engaging the plunger rod and arranged to lean against the proximal edge of the barrel so as to prevent a relative movement of the plunger rod with respect to the barrel; and
(d) a needle guard comprising a trigger portion, said needle guard being configured in sliding engagement with respect to the barrel so as to define a first position in which the needle guard covers the injection needle and a second position in which the needle guard does not cover at least a portion of the injection needle;

wherein the trigger portion is adapted to disengage the injection lock from the plunger rod when the needle guard moves from the first position to the second position, in order to allow a relative movement of the plunger rod with respect to the barrel.

The plunger rod may then move distally with respect to the barrel, thereby pushing the stopper toward the injection needle and performing the injection step. Preferably, the trigger portion is adapted to disengage the injection lock during an end portion of the movement from the first position to the second position, for example in the last 20% of the movement, in the last 10% or in the last 5% of the movement.

Thanks to the injection lock engaging the plunger rod and leaning, directly or indirectly, against a proximal edge of the syringe, the injection step cannot start before the end of the needle pricking step and the number of failed administrations is thus minimized. In addition, the disengagement of the injection lock is reliable thanks to the direct contact with the trigger portion of the needle guard. Finally, the present medical injection system is inexpensive and simple to manufacture.

For example, the injection lock may be arranged to lean directly against the proximal edge of the barrel, i.e. the injection lock may be arranged to contact the proximal edge of the barrel. Alternatively, the injection lock may be arranged to lean against an intermediate part, for example against an intermediate ring, which contacts or leans against the proximal edge of the barrel.

Preferably, the injection lock is configured to prevent any relative movement of the plunger rod with respect to the barrel, i.e. to lock the barrel and the plunger rod. In addition, the injection lock is preferably arranged around i.e. coaxially on the plunger rod in order to reduce the size of the injection system. In addition, the movements of the needle guard such as the movement from the first position to the second position of the needle guard are preferably linear or with a few degrees rotation. For example, the movements are substantially aligned along a longitudinal axis of the medical injection system or along an axis slightly shifted from the longitudinal axis of the medical injection system. This allows to simplify manufacturing and assembly of the present medical injection system.

Preferably, the injection lock and the needle guard comprise second position locking means adapted to be engaged in the second position of the needle guard in order to prevent at least a distal movement of the needle guard with regard to the injection lock. This allows to maintain the needle guard in the second position into which the injection lock is disengaged from the plunger rod and the injection needle is not covered by the needle guard. In addition, a user may change an injection site during the injection step for example in case of inconvenience or pain during the injection step. For example, the second position locking means are only engaged in the second position of the needle guard and not in the first and third positions of the needle guard.

Preferably, the trigger portion comprises a rigid leg extending proximally from the needle guard, thus allowing a compact and simple to manufacture medical injection system. Alternatively, a protrusion or a hook may extend radially from an internal surface of the needle guard.

In a preferable embodiment, the needle guard comprises a distal portion and a proximal portion provided with the trigger portion and the distal portion is movable relative to the proximal portion, preferably through a slidable engagement.

Thanks to the needle guard comprising two different portions in sliding engagement, the length of the needle guard can be adjusted and thus the length of the stroke of the needle guard with respect to the barrel between the first position and the second position can be adjusted. Consequently, the length of the injection needle uncovered in the second position and inserted into the patient's body can be adjusted.

Preferably, the needle guard is provided with releasable latching means adapted to prevent movement of the distal portion with respect to the proximal portion and the releasable latching means thus define stable or blocked positions of the distal portion with respect to the proximal portion.

Preferably, the needle guard can be moved from the second position to a third position in which the needle guard covers the injection needle. This third position allows the injection needle to be hidden from the view of the patient and to limit undesired needle pricking.

In a preferable embodiment, the medical injection system comprises a seat portion fixed to the barrel, which allows a stable positioning of the syringe inside the medical injection system.

In a preferable embodiment, the medical injection system comprises a biasing member placed between the seat portion and the needle guard in order to move the needle guard from the second position to the third position. This allows automatic covering of the injection needle as soon as the medical injection system is withdrawn from the patient's body when the second position locking means are not engaged. For example, the second position locking means remain engaged under the force of the biasing member.

Preferably, the medical injection system comprises blocking means configured to prevent movement of the needle guard relative to the barrel and/or relative to the hollow body in the third position. The third position is then a safety position in which undesired needle pricking is prevented and in which the medical injection system can be disposed safely after use.

In a preferable embodiment, the medical injection system comprises a hollow body fixed to the plunger rod and surrounding at least partially the plunger rod, wherein the needle guard is movable with respect to the hollow body at least in the first position. The hollow body may comprise a single body portion or two body portions or more and one of the body portions may define or comprise the plunger rod.

In a more preferable embodiment, the blocking means comprise:

a cam track provided on one of the needle guard and the hollow body, a lug provided on the other of the needle guard and the hollow body so as to engage the cam track, the cam track comprising a notch blocking the lug when the needle guard is moved from the second position to the third position, so as to define a safety position of the needle guard. Such blocking means are reliable and simple to manufacture. In addition, the cam track may also prevent or limit a rotational movement of the needle guard relative to the plunger rod and/or the syringe, for example, to at most 15°, preferably at most 10°, again preferably at most 5° or 3°. This results in substantially linear movements of the needle guard.

In a preferable embodiment, one of the injection lock and the plunger rod comprises a groove and the other of the injection lock and the plunger rod comprises a flexible arm engaged into the groove when the needle guard is in the first position, wherein the trigger portion is adapted to disengage the flexible arm from the groove when the needle guard moves from the first position to the second position. For example, the flexible arm comprises an abutment surface or an abutment slope adapted to bend the flexible arm out of the groove upon a proximal pressure applied by the trigger portion.

Preferably, the injection lock and the needle guard comprise second position locking means adapted to be engaged in the second position of the needle guard in order to prevent at least a proximal movement of the injection lock with respect to the needle guard. Self-administration with such a medical injection system is more convenient and more reliable since the syringe cannot have any proximal movement during the injection step.

For example, the second position locking means comprises at least one flexible leg provided on one of the injection lock and the needle guard and at least one recess provided on the other of the injection lock and the needle guard, the recess being adapted to receive at least part of the flexible leg, for example a stepped portion of the flexible leg, in the second position of the needle guard. Such second position locking means are simple to manufacture and reliable.

For example, the recess is provided onto the needle guard or onto the proximal portion of the needle guard and the flexible leg is provided onto the injection lock. Preferably, two recesses and two flexible legs are provided, for example symmetrically around a longitudinal axis of the medical injection device in order to ensure a reliable injection step.

In a preferable embodiment, the medical injection system further comprises disengagement means adapted to disengage the second position locking means during a distal movement of the plunger rod relative to the barrel.

Preferably, the disengagement means comprise at least one distal protrusion and preferably two distal protrusions fixed with respect to the plunger rod and adapted to bend the flexible leg in order to disengage the flexible leg from the recess, during a distal movement of the plunger rod with respect to the barrel. For example, the at least one distal protrusion is provided inside the hollow body, such as protruding from an internal distal surface of the hollow body.

Consequently, at the end of the injection operation a movement between the needle guard and the syringe is allowed again, in particular a distal movement of the needle guard, and the needle guard may cover the injection needle after the injection operation in the third position of the needle guard. The disengagement may occur during an end portion of the distal movement of the plunger rod, i.e. at the end period of the injection operation such that the last 20% of the movement of the plunger rod, the last 10% or the last 5%.

For example, the needle guard is adapted to surround at least partially the seat portion and the hollow body may be adapted to surround at least part of the needle guard, thus allowing an optimal protection of the syringe and/or a medical injection system convenient to use.

BRIEF DESCRIPTION OF THE DRAWINGS

Further advantages and preferred embodiments of the present disclosure will become apparent from the following detailed description and drawings, in which:

FIGS. 7A-7C are lateral view of a medical injection system according to another embodiment of the present disclosure, wherein FIGS. 7B-7C are cross-section views of this medical injection system in a first position.

DETAILED DESCRIPTION

The present medical injection system is intended for administration of parenteral drug compositions by a medical caregiver or preferably by a patient with a simplified operation.

As such, in the present disclosure, the distal direction must be understood as the direction of injection with reference to the medical injection system, and the proximal direction is the opposite direction, i.e. the direction toward the hand of the medical caregiver or of the patient. In addition, a drug composition must be understood as all kinds of injectable drug composition adapted for therapeutics, aesthetics, preventive or diagnosis applications.

Figure 1:
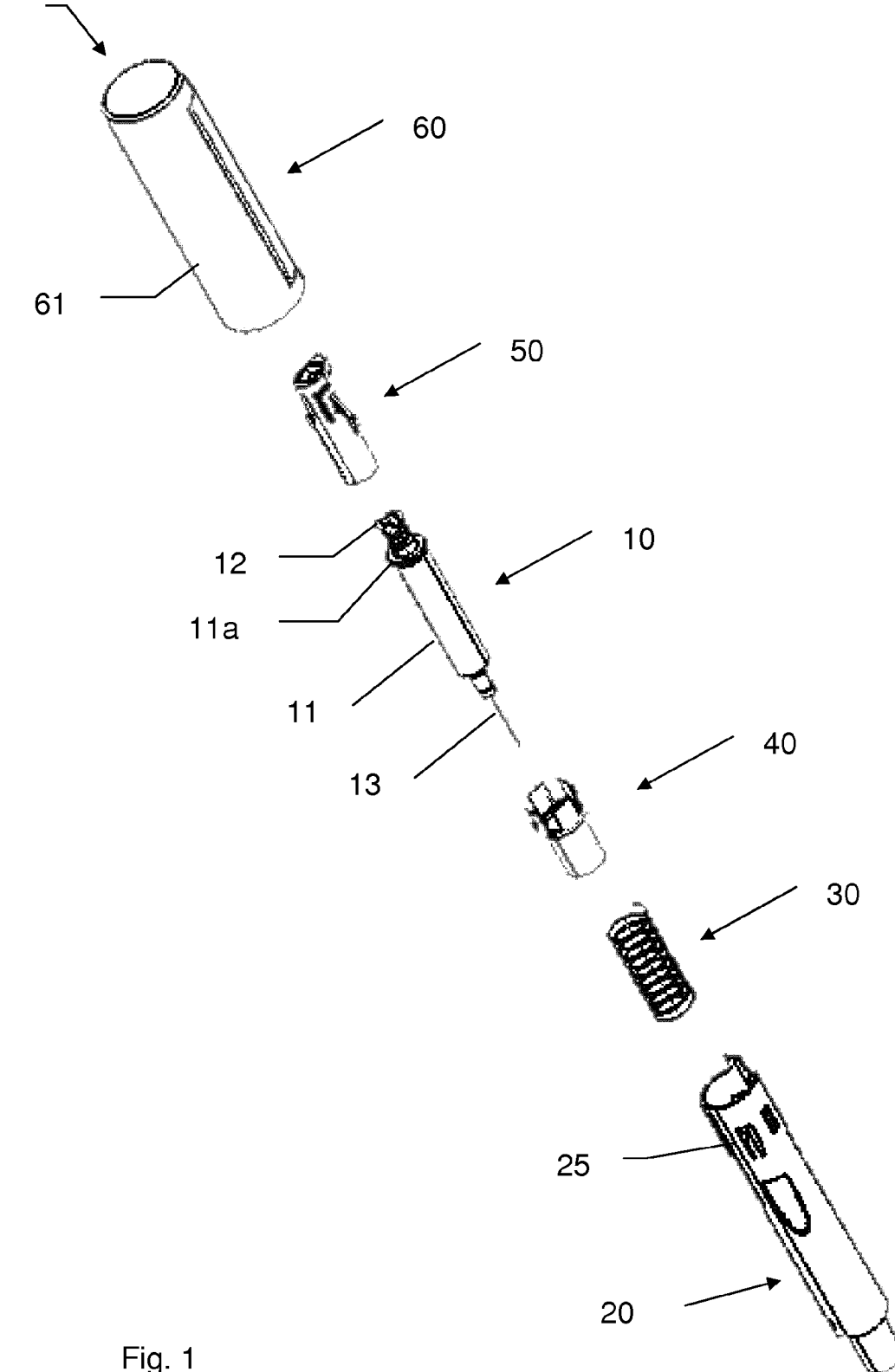
FIG. 1 is an exploded view of a medical injection system according to an embodiment of the present disclosure.

Now regarding FIG. 1, a medical injection system 1 according to the present disclosure shown in an exploded view comprises a syringe 10, a needle guard 20, a biasing member 30, a seat portion 40, an injection lock 50 and a hollow body 60. The hollow body 60 comprises a peripheral wall 61, a plunger rod 63 (visible in FIGS. 2B-2C) and optionally a cam track 65 (visible in FIGS. 6A-6B). The needle guard 20 may comprise a lug 25 intended to be in a sliding engagement within the cam track 65. In addition, the syringe 10 is provided with a barrel 11 having a proximal edge 11a for example in the form of a flange, a stopper 12 in sliding engagement inside the barrel 11 and an injection needle 13.

Figure 2A:
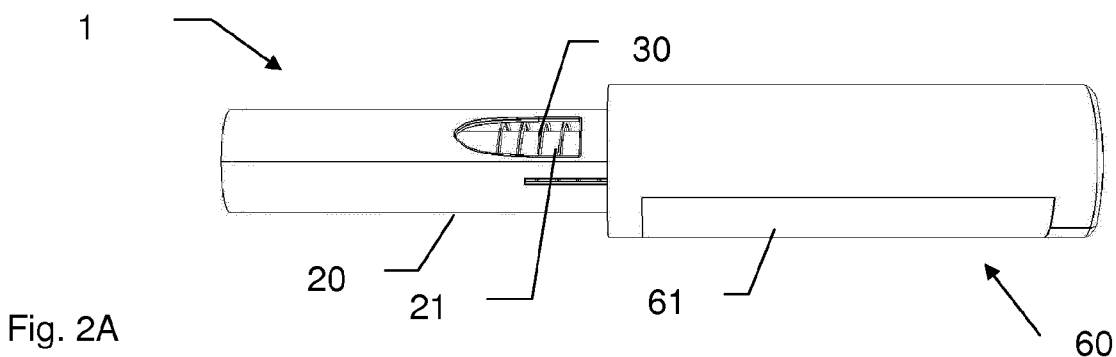
FIG. 2A is a lateral view of the medical injection system according to FIG. 1 in the first position and FIGS. 2B and 2C are two lateral cross-section views of the medical injection system according to FIG. 1 in the first position.
Figure 2B:
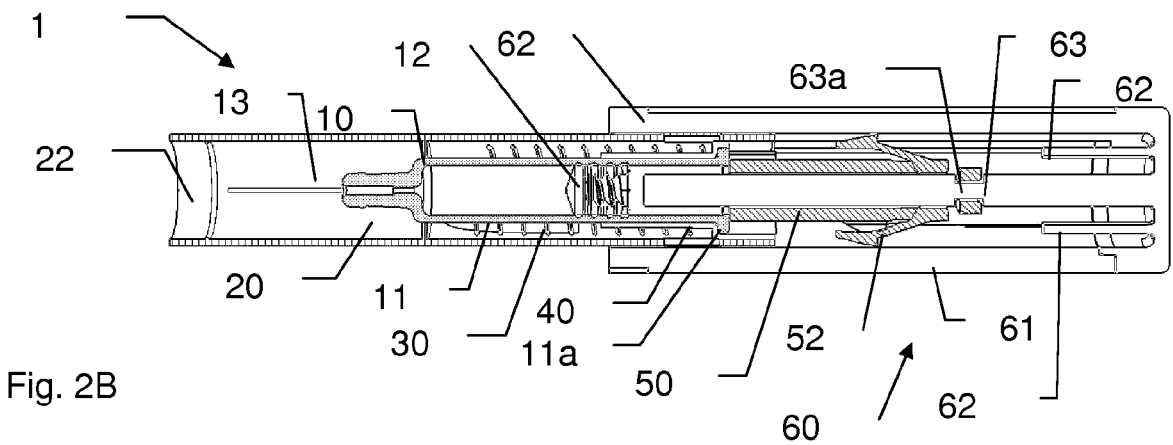
Figure 2C:
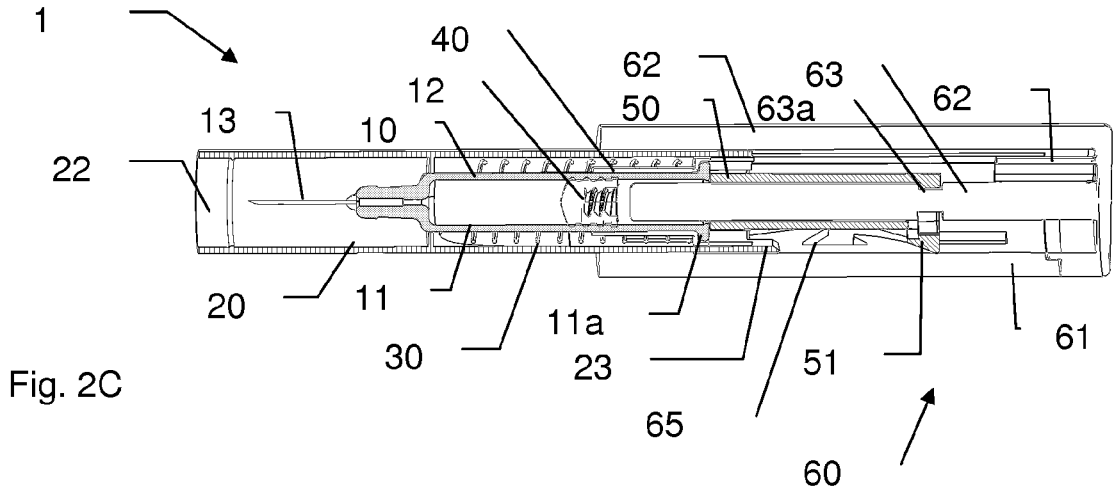

In FIGS. 2A to 2C, the medical injection system 1 is shown assembled in a first position. The needle guard 20 is mounted in sliding engagement with the hollow body 60. The needle guard 20 may comprise a window 21 allowing the biasing member 30 and the syringe 10 to be seen and thus providing a visual control of the state or the position of the medical injection system 1. In addition, the needle guard 20 comprises an open distal end 22 and a rigid leg 23 extending proximally and longitudinally from the needle guard 20 (visible in FIG. 2C). In a storage position not represented, a cap may cover the needle.

Now more particularly with reference to FIGS. 2B and 2C, the syringe 10 is received in the seat portion 40. The seat portion 40 contacts a distal surface and/or a lateral surface of the proximal edge 11 a or of the flange of the syringe 10 and prevents a distal movement of the syringe 10 with regard to the seat portion 40.

The biasing member 30 is located between the seat portion 40 and an abutment of the needle guard 20 in order to push the needle guard 20 in the distal direction (the left direction of the figures). The engagement of the lug 25 and the cam track 65 may prevent disengaging the needle guard 20 from the hollow body 60 (see FIGS. 6A-6C).

On the proximal end of the medical injection system 1 (on the right side of the figures), the hollow body 60 defines a peripheral wall 61, the peripheral wall 61 surrounding the plunger rod 63 which is provided with a groove 63a. The plunger rod 63 is in pushing engagement with the stopper 12. Consequently, a distal movement of the hollow body 60 relative to the syringe 10 results in a distal movement of the stopper 12 relative to the barrel 11, thus expelling the content (i.e. the drug composition) of the barrel 11 through the injection needle 13. Further, the internal distal surface of the hollow body 60 may comprise at least one protrusion or preferably two protrusions 62 protruding longitudinally from the internal distal surface.

The injection lock 50 may be a cylinder, a tube or a rod and is placed against and/or preferably around the plunger rod 63. It comprises at least a flexible arm 51 engaging the groove 63a of the plunger rod 63 and the flexible arm 51 and the groove 63a thus act as engagement means allowing the engagement of the injection lock 50 with the plunger rod 63. The distal portion of the injection lock 50 rests or leans directly or indirectly against the proximal edge 11a of the barrel 11. Consequently, in the first position shown in FIGS. 2A-2C, the injection lock prevents any movement of the plunger rod 63 with regard to the barrel 11 and thus prevents the movement of the stopper 12 required for the injection step. The injection lock 50, the flexible arm 51, the groove 63a and the proximal edge 11 a thus act as first position locking means preventing any injection step in the first position of the medical injection system 1. The injection lock 50 further comprises at least one and preferably two flexible legs 52 extending radially from the injection lock 50.

The first position shown in FIGS. 2A-2C represents a start position in which the medical injection system is ready for the administration of a drug composition to a patient. To perform the first step, i.e. the needle-pricking step, the patient may press the open distal end 22 of the needle guard 20 against the skin on an injection area and push the hollow body 60 toward the skin. The plunger rod 63 and the hollow body 60 cannot move relative to the syringe 10, thanks to the injection lock 50, so that no injection can be performed at this stage. Consequently, only the needle guard 20 can slide relative to the syringe 10 and the hollow body 60, resulting in uncovering the injection needle 13 which then protrudes from the open distal end 22 and can penetrate the patient's skin to perform the needle pricking step.

Figure 3A:
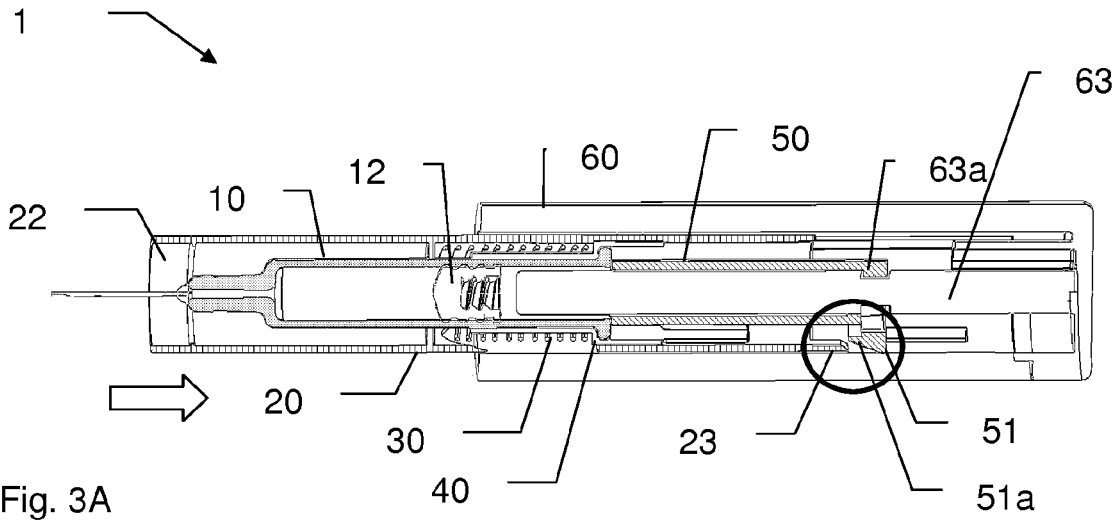
FIGS. 3A and 3B are cross-section views of the medical injection system according to FIG. 1 in a second position, or at an end portion of a movement between the first position and the second position.
Figure 3B:
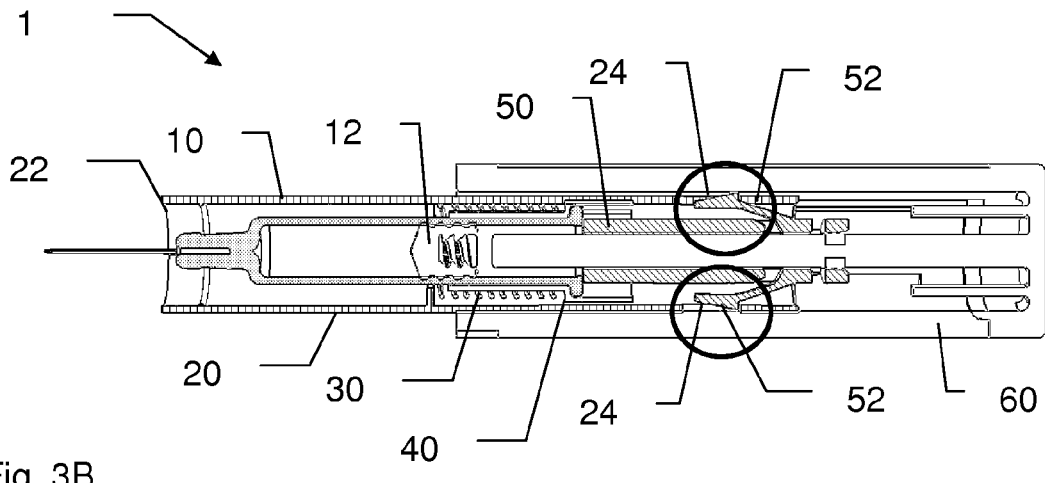

In FIGS. 3A-3B, the medical injection system 1 is at the end of the needle pricking step or at the end portion of the needle pricking step: the injection needle 13 is introduced into the patient's body, the needle guard 20 has travelled proximally with regard to the hollow body 60 and the biasing member 30 is compressed by the needle guard 20 against the seat portion 40. In an end portion of the proximal movement of the needle guard 20 relative to the hollow body 60, the rigid leg 23 comes in contact with a sloping surface 51a of the flexible arm 51 of the injection lock 50 (see the circled area in FIG. 3A) and applies a proximal pressure on the flexible arm 51 which bends the flexible arm 51 out of the groove 63a.

Consequently, thanks to the interaction of the rigid leg 23 acting as a trigger portion, the engagement means are unlocked and the injection may be triggered. In detail, the flexible arm 51 is disengaged from the groove 63a of the plunger rod 63, by a radial and/or proximal movement of the flexible arm 51. The injection lock 50 is then disengaged from the plunger rod 63 and the plunger rod 63 is now movable with regard to the syringe 10, in a second position of the medical injection system 1.

In the same movement, the flexible legs 52 of the injection lock 50 and for example stepped extremities of the flexible legs 52 are accommodated and locked in recesses 24 of the needle guard 20, as visible in the circled areas of FIG. 3B. The injection lock 50 is thus disengaged from the plunger rod 63 and engaged with the needle guard 20 and the flexible legs 52 and the recesses 24 acts as second position locking means. Consequently, the second position of the medical injection system is locked and the syringe 10 is prevented from moving proximally in the second position of the medical injection system 1, for example under the force of the biasing member 30. In addition, a distal movement of the needle guard 20 is prevented with regard to the injection lock 50 and the syringe 10 and the injection lock 50 cannot reengaged the plunger rod 63. Finally, a movement of the hollow body 60 and thus of the plunger rod 63 with regard to the syringe 10 is now possible, thus allowing the injection step to be performed.

Under the distal force applied by the patient onto the hollow body 60, the plunger rod 63 pushes the stopper 12 in a distal movement inside the barrel 11. The content of the barrel 11 such as a drug composition is expelled through the injection needle 13 into the patient's body and the injection step is performed.

Figure 4:
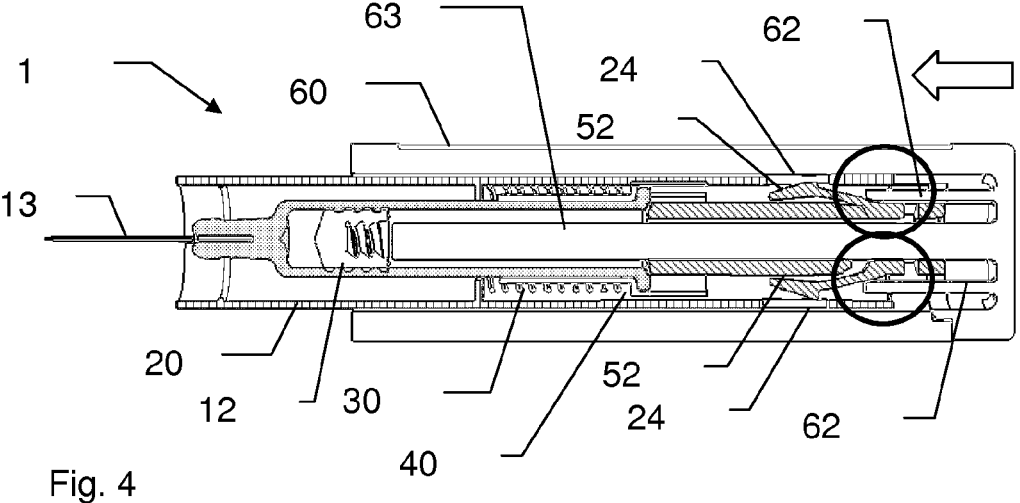
FIG. 4 is a cross-section view of the medical injection system according to FIG. 1 after an injection step has been performed, or at an end portion of the injection step movement.

In FIG. 4, at the end of the injection step, for example at an end portion of the distal movement of the hollow body 60 with regard to the needle guard 20, the distal protrusions 62, fixed relative to the plunger rod 63, come into abutment with the flexible legs 52. For example, the distal protrusions 62 come in contact with a sloping surface of the flexible legs 52 and the flexible legs 52 are deflected radially toward the plunger rod 63 so as to be disengaged from the recesses 24 of the needle guard 20, as visible in the circled areas of FIG. 4. The distal protrusions 62 thus act as disengagement means to unlock the second position locking means and may consist of any other adapted technical means such as a ring or one or several circular protrusions. Consequently, the injection lock 50 is not locked anymore to the needle guard 20 and a relative movement, in particular a distal movement of the needle guard 20 with regard to the syringe 10 is now possible. In the same time, the stopper 12 may reach the distal end of the barrel 11, thus completing the injection step.

After the end of the injection step, for example when the stopper 12 reaches the distal end of the barrel 11 and/or immediately after the position of the medial injection system 1 shown in FIG. 4, the patient may stop applying a distal pressure on the hollow body 60 and may withdraw the medical injection system 1 from his body. The needle guard 20 is now free to move relative to the syringe 10 thanks to the disengagement of the second position locking means and the biasing member 30 applies a distal pressure on the needle guard 20 and/or a proximal pressure on the seat portion 40 in order to move the needle guard 20 in the distal direction with respect to the syringe 10 and the hollow body 60.

Figure 5:
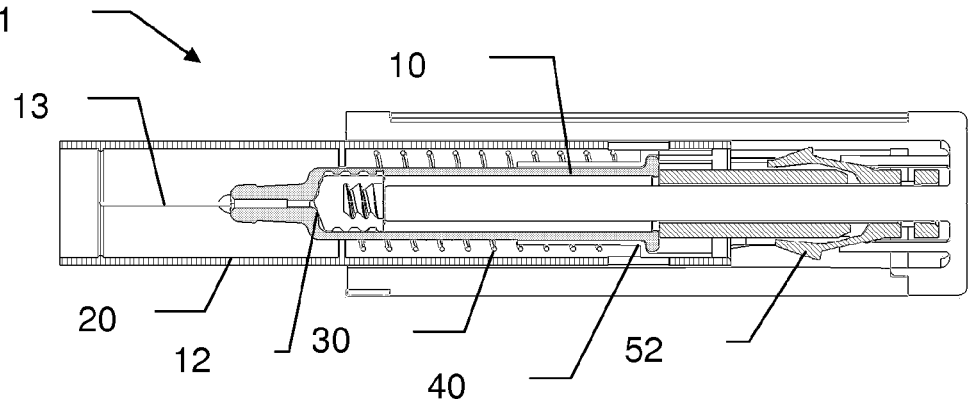
FIG. 5 is a cross-section view of the medical injection system according to FIG. 1 in a third position.

As represented in FIG. 5, the needle guard 20 has moved distally relative to the syringe 10 in a third position in which the needle guard 20 covers the injection needle 13. In this third position, blocking means may permanently block any movement of the needle guard 20 with regard to the plunger rod 63 and thus with regard to the syringe 10. The needle guard 20 then permanently covers the injection needle 13 and the third position is a safety position allowing a safe disposal of a medical injection system 1 after use.

Figure 6A:
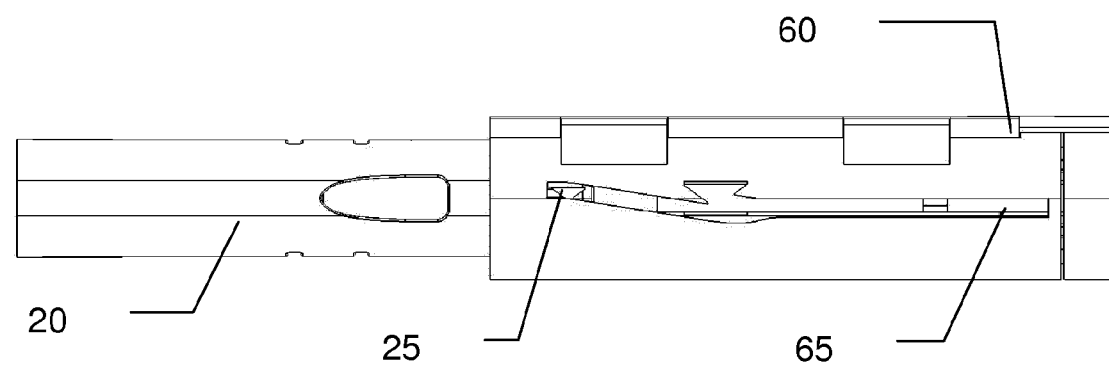
FIGS. 6A-6C are lateral view of a medical injection system according to FIG. 1 in the first, second and third position, respectively.
Figure 6B:
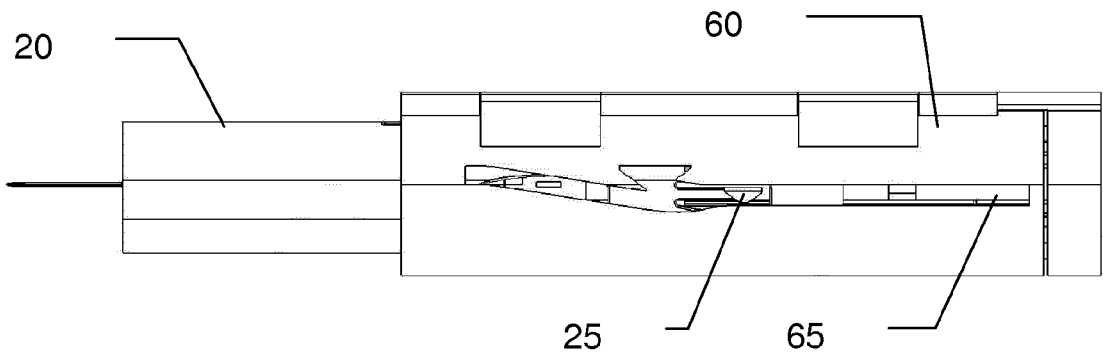
Figure 6C:
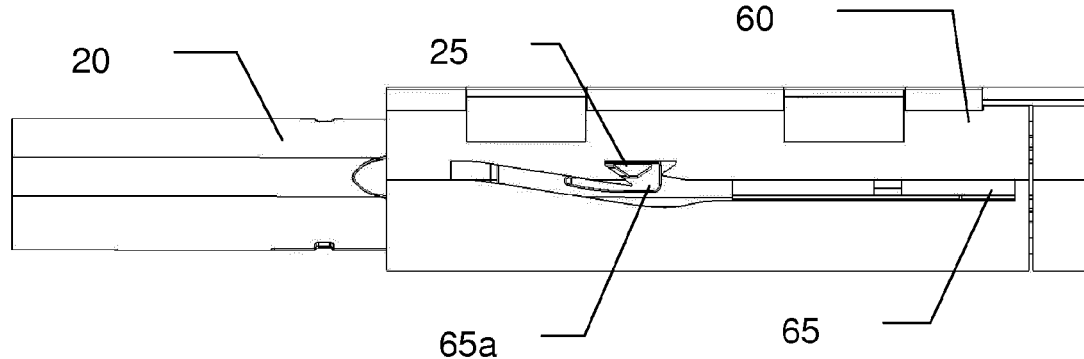

Considering FIGS. 6A-6C, an example of the blocking means may comprise the cam track 65 provided onto the hollow body 60 and may be engaged by the lug 25 of the needle guard 20. In the first position of the medical injection system 1, the lug 25 is located in a distal portion of the cam track 65 (see FIG. 6A) and may prevent disassembly of the needle guard 20 from the hollow body 60, in the case a distal pressure is applied on the needle guard 20. In the second position (see FIG. 6B), the lug 25 has slid from the distal extremity, for example to a median portion or a proximal portion of the cam track 65 and may allow an optimal guidance of the sliding movement of the needle guard 20 from the first position to the second position. In the third position (see FIG. 6C), the lug 25 is blocked in a notch 65a of the cam track 65 and due to that, the needle guard 20 is blocked with regard to the hollow body 60 and the syringe 10. The lug 25 and the cam track 65, or at least the notch 65a are thus an example of blocking means to block the present medical injection system in a safety position. Alternatively, they can adopt any other adapted shape or geometry.

To sum up the kinematic of the medical injection system according to the present disclosure, in the first position the syringe 10, the plunger rod 63 and the hollow body 60 are fixed by the first position locking means, while the needle guard 20 is movable with respect to the hollow body 60 and the syringe 10. In the second position, the first position locking means are disengaged so that the plunger rod 63 and the hollow body 60 are movable relative to the syringe 10, while the second position locking means prevent any movement or at least any proximal movement of the syringe 10 relative to the needle guard 20. In the third position, the second position locking means have been disengaged, the needle guard 20 may have been placed in a distal position around the needle 13 and blocking means may block any movement of the needle guard 20 relative to the syringe 10 and the needle 13.

The medical injection system according to the present disclosure allows at least the injection step to be blocked as long as the needle pricking step is not completed. Consequently, the medical injection system 1 allows a more convenient and safer administration of a drug composition and minimizes the risk of failed administration. In addition, the medical injection system 1 comprises a low number of elements and is simple to manufacture.

Now regarding FIGS. 7A to 7C, a medical injection system 100 according to another embodiment of the present disclosure is identical to the medical injection system 1 previously described with the differences below.

In particular, the needle guard 120 of the medical injection system 100 comprises two distinct elements: a distal element 120a and a proximal element 120b, wherein the distal element 120a and the proximal element 120b are in sliding engagement one with the other.

The distal element 120a of the needle guard 120 may be provided with one or preferably two slots 125 each provided with at least two notches 125a, 125b aligned on a longitudinal axis of the medical injection system 100. The proximal element 120b of the needle guard 120 may comprise one or preferably two pegs 126 each adapted to be received in one of the notches 125a, 125b in a stable position.

For example, the pegs 126 are mounted on flexible portions of the proximal element 120b and can be disengaged from one the notches 125a, 125b by a radial pressure. Consequently, the notches 125a, 125b and the pegs 126 act as releasable latching means in order to prevent an undesired movement of the distal element 120*a* relative to the proximal element 120*b*, in particular when the medical injection system 100 is in used.

In addition, a rigid leg 123 (see FIG. 7C) is provided on the proximal element 120*b* and this rigid leg 123 is intended to act as a trigger portion in order to disengage the flexible arm 151 of the injection lock 150 from the groove 163*a* of the plunger rod 163. In addition, recesses 124 may also be provided onto the proximal element 120*b* in order to be engaged by the flexible arms 152 of the injection lock 150 in the second position of the medical injection system 100.

Figure 7A:
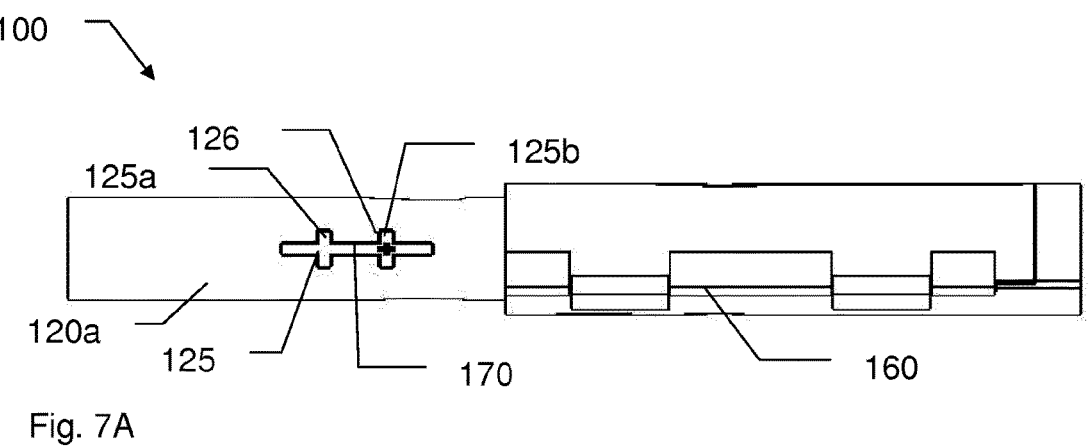
Figure 7B:
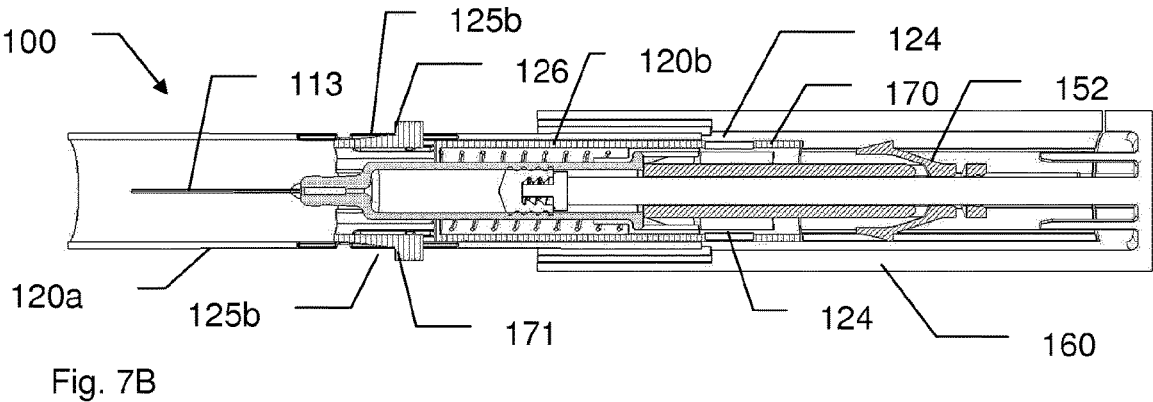
Figure 7C:
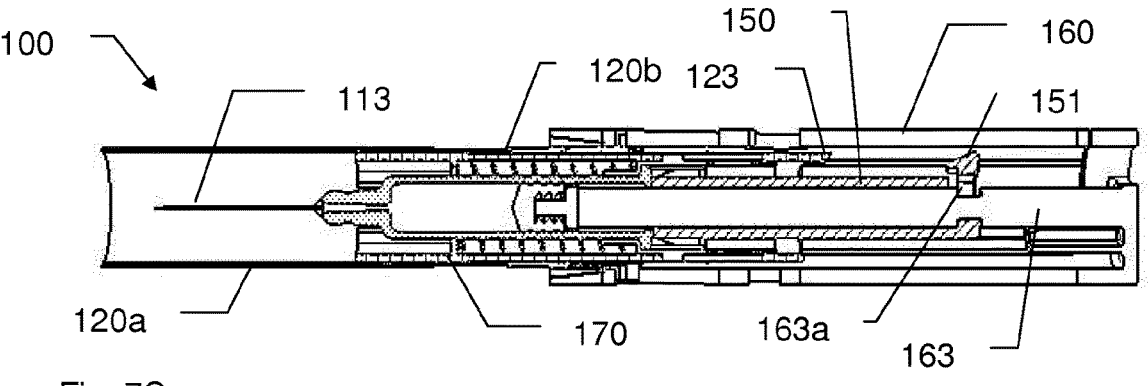

Thanks to the distal element 120*a* in sliding engagement with the proximal element 120*b*, the length of the needle guard 120 in the exemplary FIGS. 7A-7C can be adjusted between two different lengths. Consequently, the distance between the rigid leg 123 and the flexible arm 151 in the first position can be modified and thus the length of the stroke of the needle guard 120 with regard to the hollow body 160.

By changing the length of the needle guard 120, it is possible to modify the uncovered length of the injection needle 113 in the second position and thus the length of the injection needle 113 that is inserted into the skin during the needle pricking step. Consequently, the injection depth can be adjusted by the patient or by the medical staff according to the area or the type of injection.

Although the present disclosure has been described and illustrated in detail, it is clearly understood that the same is by way of illustration and example only and is not to be taken by way of limitation, the scope of the present disclosure being limited only by the terms of the appended claims.

In particular, the biasing member may be any biasing member known by the skilled person, such as any type of spring. The injection lock, the needle guard, the hollow body and the seat portion may have all adapted shape. In addition, the first position locking means may have any geometry or configuration as long as the injection lock 50 engages the plunger rod and leans directly or indirectly against the barrel. For example, the injection lock may have a groove and the plunger rod may have a flexible arm engaging the groove. Alternatively, the flexible leg could be replaced by a locking clip and the groove by recesses. In addition, the trigger portion of the needle guard may be any abutment surface adapted to disengage the flexible arm from the groove. Finally, the injection lock could engage the hollow body instead of engaging the plunger rod.

Similarly, the second position locking means may also have any geometry or configuration adapted to block a proximal translation of the syringe with regard to the needle guard when the injection step is performed. The blocking means can also show all possible configuration or geometry known by the skilled person in order to prevent any movement of the needle guard with regard to the syringe in the third position of the medical injection system. The releasable latching means may also be different from the slot 125, the notches 125*a* and 125*b* and the peg 126 shown in FIGS. 7A-7C. For example, more than two notches may be provided.

Further, the hollow body 60 can consist in a single body portion or more than two body portions. The medical injection system may have any cross-section such as square, oval or triangular. In the second embodiment, one or more than two notches may be provided, with one or more than two pegs. Finally, the syringe is preferably pre-filled before or during the assembly of the medical injection system.

The invention claimed is:

1. A medical injection system comprising:
   (a) a syringe provided with:
      (i) a barrel having a proximal-most edge;
      (ii) a stopper in sliding engagement inside the barrel; and
      (iii) an injection needle;
   (b) a plunger rod in pushing engagement with the stopper,
   (c) an injection lock engaging the plunger rod wherein a distalmost edge of the injection lock is arranged to lean against the proximal-most edge of the barrel so as to prevent a relative movement of the plunger rod with respect to the barrel; and
   (d) a needle guard comprising a rigid leg configured as a trigger portion, said needle guard being configured in sliding engagement with respect to the barrel so as to define a first position in which the needle guard covers the injection needle and a second position in which the needle guard does not cover at least a portion of the injection needle;
   wherein the plunger rod comprises a groove and the injection lock comprises a flexible arm engaged into the groove when the needle guard is in the first position,
   wherein the rigid leg is adapted to contact the flexible arm of the injection lock to disengage the flexible arm from the groove of the plunger rod when the needle guard moves from the first position to the second position, in order to allow a relative movement of the plunger rod with respect to the barrel, and
   wherein the injection lock and the needle guard comprise second position locking means adapted to be engaged in the second position of the needle guard in order to prevent at least a distal movement of the needle guard with regard to the injection lock and prevents a proximal movement of the injection lock with respect to the needle guard, wherein the medical injection system comprises disengagement means fixed with respect to the plunger rod adapted to disengage the second position disengagement means during a distal movement of the plunger rod relative to the barrel, wherein the second position locking means comprises at least one leg provided on one of the injection lock and the needle guard and at least one recess provided on the other of the injection lock and the needle guard, and wherein the disengagement means comprise at least one protrusion positioned on a distal end of the plunger rod.

2. The medical injection system according to claim 1, wherein the needle guard comprises a distal portion and a proximal portion provided with the trigger portion and wherein the distal portion is movable relative to the proximal portion.

3. The medical injection system according to claim 2, wherein the needle guard is provided with releasable latching means adapted to prevent movement of the distal portion of the needle guard with respect to the proximal portion of the needle guard.

4. The medical injection system according to claim 1, wherein the needle guard can be moved from the second position to a third position in which the needle guard covers the injection needle.

5. The medical injection system according to claim 1, further comprising a seat portion fixed to the barrel.

6. The medical injection system according to claim 5, further comprising a biasing member placed between the seat portion and the needle guard in order to move the needle guard from the second position to a third position.

7. The medical injection system according to claim 4, further comprising blocking means configured to prevent a movement of the needle guard relative to the barrel in the third position.

8. The medical injection system according to claim 1, further comprising a hollow body fixed to the plunger rod and surrounding at least partially the plunger rod, wherein the needle guard is movable with respect to the hollow body at least in the first position.

9. The medical injection system according to claim 8, wherein the blocking means comprise:

a cam track provided on one of the needle guard and the hollow body a lug provided on the other of the needle guard and the hollow body so as to engage the cam track, the cam track comprising a notch blocking the lug when the needle guard is moved from the second position to the third position, so as to define a safety position of the needle guard.

10. The medical injection system according to claim 1, wherein the at least one recess is provided on a proximal portion of the needle guard.

11. The medical injection system according to claim 5, wherein the needle guard is adapted to surround at least partially the seat portion.

12. The medical injection system according to claim 8, wherein the hollow body is adapted to surround at least partially the needle guard.

13. The medical injection system according to claim 7, further comprising a hollow body fixed to the plunger rod and surround at least partially the plunger rod, wherein the needle guard is movable with respect to the hollow body at least in the first position.

14. The medical system according to claim 2, wherein the second position locking means are further adapted to be engaged in the second position of the needle guard in order to prevent a proximal movement of the injection lock with respect to the needle guard.

\* \* \* \* \*